US00PP08837P

United States Patent [19]

Austin

[11] Patent Number: Plant 8,837

[45] Date of Patent: Jul. 19, 1994

[54] ROSE PLANT AUSLILAC

[75] Inventor: David C. H. Austin, Wolverhampton, England

[73] Assignee: David Austin Roses Limited, Albrighton, England

[21] Appl. No.: 26,546

[22] Filed: Mar. 4, 1993

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Klarquist Sparkman Campbell Leigh & Whinston

[57] ABSTRACT

A *Rosa hybrida* shrub rose plant is disclosed having distinctive, lilac-colored flowers; double flowers with rosette center; strong fragrance; and healthy, bushy growth.

1 Drawing Sheet

The present invention relates to a new and distinct variety of rose plant (*Rosa hybrida*) of the shrub class which was originated by me by crossing an unnamed seedling, a plant with upright growth to about 1.4 meters, with apricot semi-double flowers, with the variety "Hero" (unpatented), having rather straggly, shrub-like growth to a plant 1.2 meters high by 1 meter wide, with pure pink, deeply cupped, fragrant flowers.

The primary objective of this breeding was to produce a new rose variety having the repeat flowering of its parents with old-fashioned-type flowers. The objective was substantially aachieved along with other desirable improvements as evidenced by the following unique combination of characteristics which are outstanding in the new variety and which distinguish it from its parents, as well as from all other varieties of which I am aware:

1. Distinctive, lilac-colored flowers;
2. Double flowers with rosette center;
3. Strong fragrance; and
4. Healthy bushy growth.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—"Hero" variety.

Classification:

*Botanical.*—*Rosa hybrida.*

*Commerical.*—Shrub.

FLOWER

Observations made from specimens grown a garden environment in Albrighton, Wolverhampton, England, in Aug. 1992.

Blooming habit: Recurrent.

Bud:

*Size.*—About 2 to 3 cm long when the petals start to unfurl.

*Form.*—Short, pointed ovoid.

*Color.*—When sepals first divide, bud color is Red-Purple Group 67A. When half blown, the upper sides of the petals are Red-Purple Group 63C (center) to 63D (edge); and the lower sides of the petals are Red-Purple Group 63D (center) to 62D (edge).

*Sepals.*—Color: Yellow-Green Group 144A/B. Surface texture: Slightly leathery. There are three normally appendaged sepals. There are two unappendaged sepals with smooth edges.

*Receptacle.*—Color: Yellow-Green Group 144B. Shape: Goblet. Size: Medium, about 6–7 mm×7–8 mm. Surface: Smooth, slightly glandular.

*Peduncle.*—Length: Long, averaging about 5–7 cm. Surface: Glandular. Color: Medium green. Strength: Erect.

Bloom:

*Size.*—Medium. Average open size is 6 to 7 cm inches.

*Borne.*—Singly or a few together, in clusters having irregular shape.

*Stems.*—Medium length, normal strength. Average length is about 1 m.

*Form.*—When first open: Globular. Permanence: Flattens, outer petal edges curl slightly.

*Petalage.*—Number of petals under normal conditions: 50–70, decreasing as the season progresses, the petal size also decreasing. No petaloids are formed.

*Color.*—The upper side of the petals is Red-Purple Group 63D at the edge. The reverse side of the petals is Red-Purple Group 62D at the edge. The base of petals is Red-Purple Group 63C. The major color on the upper side is Red-Purple Group 63C.

*Variegations.*—None.

*Discoloration.*—The general tonality at the end of the first day: Slightly paler. At the end of the third day: Red-Purple Group 62D.

*Fragrance.*—Strong fruity.

Petals:

*Texture.*—Thin.
*Shape.*—Round, occasionally notched, deltoid.
*Form.*—Tips slightly recurved.
*Arrangement.*—Quartered, with few small petaloids in the center.
*Persistence.*—Petals drop off cleanly before drying.
*Lastingness.*—On the plant: 7–10 days. As a cut flower: 5–7 days.

Reproductive parts:
*Anthers.*—Size: Medium. Quantity: Many. Color: Yellow. Arrangement: Regular around styles.
*Filaments.*—Color: White.
*Pollen.*—Color: Lemon yellow.
*Styles.*—Color: Pale Green.
*Stigmas.*—Color: Yellow.
*Fertility at maturity.*—An open center develops in the flowers, permitting insect pollen vectors to reach the stigmas. Hips are occasionally formed and pinching is recommended to maintain recurrent blooming.

Form: Bush.

Growth: Medium vigor, upright. A mature plant is about 1 m tall and 0.75 m wide. Six to eight strong canes will normally develop in a mature specimen. The plant is basically dominant, but branches develop on the upper portions of the canes as well. The mid-cane internode length is 7 cm.

Foliage:
*Number of leaflets on normal mid-stem leaves.*—5.
*Size.*—Medium, about 11–13 cm.
*Quantity.*—Normal.
*Color.*—New foliage: Yellow-Green Group 144D. Old foliage: Yellow-Green Group 144D.

Leaflets:
*Shape.*—Round.
*Texture.*—Upperside: Smooth.
*Edge.*—Serrated.
*Serration.*—Double and single serrations, medium to large in size.
*Petiole rachis.*—Color: Reddish.
*Petiole underside.*—With occasional prickles.
*Stipules.*—About 1¼ inches long, glandular.
*Disease resistance.*—Resistant to mildew and black-spot under normal growing conditions at Albrighton, Wolverhampton, England.

Wood:
*New wood.*—Color: Medium green. Bark: Smooth.
*Old wood.*—Color: Green. Bark: Smooth.

Prickles:
*Quantity.*—Ordinary number on main canes from base. Ordinary number on laterals from main canes.
*Form.*—Medium length (9 to 10 mm) straight.
*Color when young.*—Brown.
*Position.*—Evenly distributed. Randomly distributed from touching to 5 cm apart.

Small prickles:
*Quantity.*—None on main stalks or on lateral stalks.

I claim:

1. A new and distinct variety of *Rosa hybrida* rose plant of the shrub class, substantially as herein shown and described, being characterized particularly as to novelty by the unique combination of its distinctive, lilac-colored flowers; double flowers with rosette center; strong fragrance; and healthy, bushy growth.

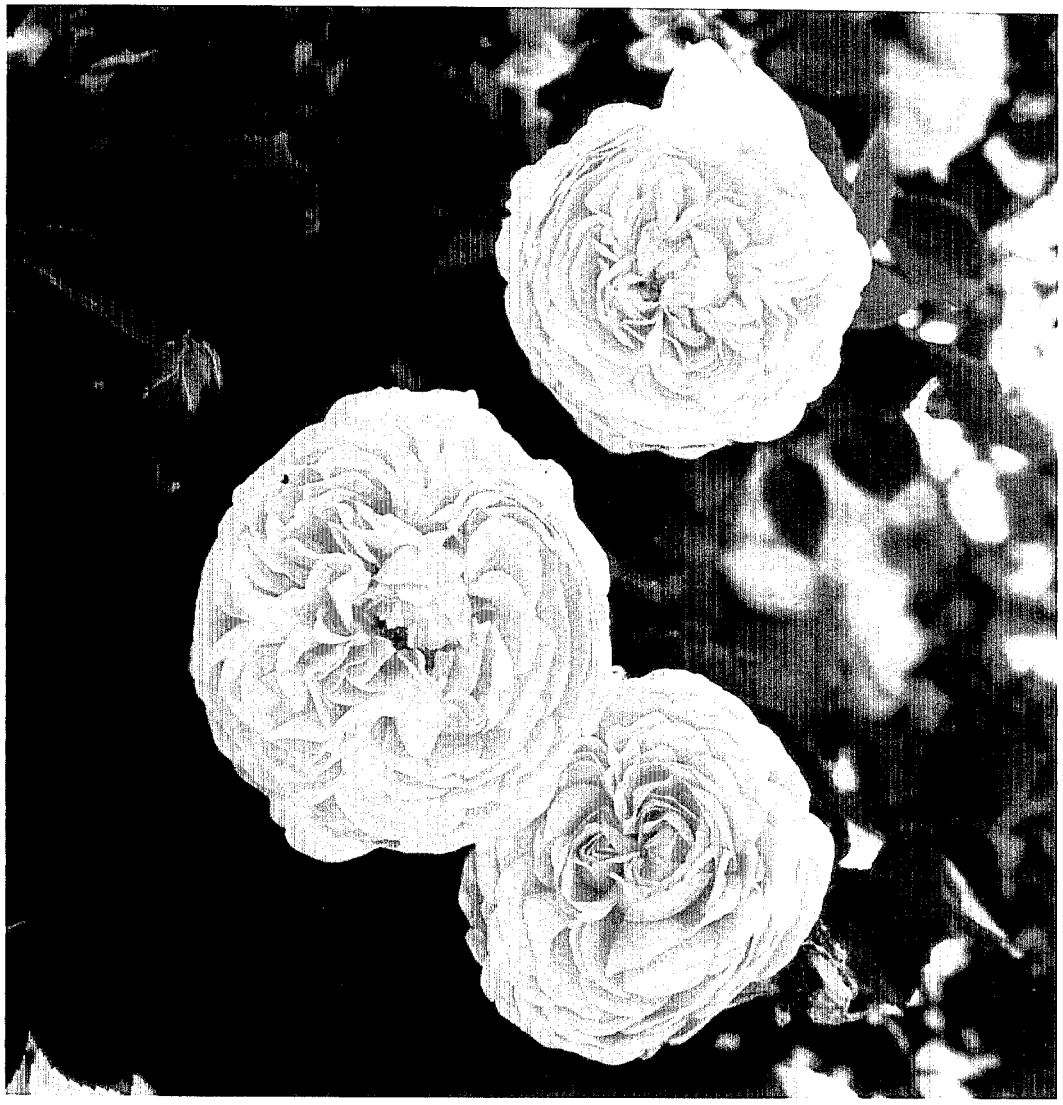

* * * * *